(12) United States Patent
Meinlschmidt et al.

(10) Patent No.: US 6,461,035 B2
(45) Date of Patent: Oct. 8, 2002

(54) DEVICE AND METHOD FOR NON-CONTACT DETECTION OF STRUCTURAL AND/OR SURFACE FAULTS IN LARGE SURFACE BODIES

(75) Inventors: Peter Meinlschmidt, Wendeburg (DE); Joerg Sembach, Moenchengladbach (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 09/834,789

(22) Filed: Apr. 13, 2001

(65) Prior Publication Data

US 2001/0050772 A1 Dec. 13, 2001

Related U.S. Application Data

(63) Continuation of application No. PCT/DE99/02453, filed on Aug. 5, 1999.

(30) Foreign Application Priority Data

Oct. 13, 1998 (DE) .......................................... 198 46 995

(51) Int. Cl.[7] .......................... G01N 21/84; G01N 21/00; G01N 25/72; G01J 5/00
(52) U.S. Cl. .......................... 374/5; 356/237.2; 356/430; 374/124; 374/57
(58) Field of Search ................................ 356/430, 429, 356/431, 237.2; 374/4, 5, 6, 7, 45, 50, 124, 55, 43, 57, 49; 250/341.6, 332

(56) References Cited

U.S. PATENT DOCUMENTS 5,959,737 A * 9/1999 Kaminaga et al. .......... 356/430
6,000,844 A * 12/1999 Cramer et al. .............. 374/124
6,013,915 A * 1/2000 Watkins .................... 250/341.1

FOREIGN PATENT DOCUMENTS

| DE | 196 28 391 C1 | 9/1997 |
|---|---|---|
| DE | 197 20 461 A1 | 2/1998 |
| DE | 197 03 484 A1 | 8/1998 |
| EP | 0 637 745 A1 | 2/1995 |
| EP | 0 813 055 A1 | 12/1997 |
| WO | WO 94/19160 | 9/1994 |

OTHER PUBLICATIONS

H. Tretout's treatise: "Composites, la thermographie ca marche en CND" Mesures, Regulation Automatisme, vol. 51, No. 15, Nov. 1986, pp. 43–46, XP002125600 Paris.*
H. Tretout's treatise: "Composites, la thermographie ça marche en CND" Mesures, Regulation Automatisme, vol. 51, No. 15, Nov. 1986, pp. 43–46, XP002125600 Paris.
Patent Abstracts of Japan, vol. 015, No. 041, Publication No. 02278146, dated Nov. 14, 1990, Mitsubishi Electric Corp., "Surface Defect Inspecting Device".

* cited by examiner

Primary Examiner—Frank G. Font
Assistant Examiner—Roy M Punnoose
(74) Attorney, Agent, or Firm—Husch & Eppenberger, LLC; Robert E. Muir

(57) ABSTRACT

A device for contactless testing of structural and/or surface defects of large-surface bodies, especially of slab-shaped materials includes a conveying device with an unsupported area; a source of heat arranged above the plane of conveyance and extending transversally to the direction of conveyance and which radiates heat in lines or strips onto the plane of conveyance; a thermographic camera having at least one camera line aligned transversally to the direction of conveyance and arranged above the plane of conveyance and after the source of heat in the direction of conveyance; and a computer connected to the camera that has a monitor and generates a separate heat image pattern from every camera line.

8 Claims, 1 Drawing Sheet

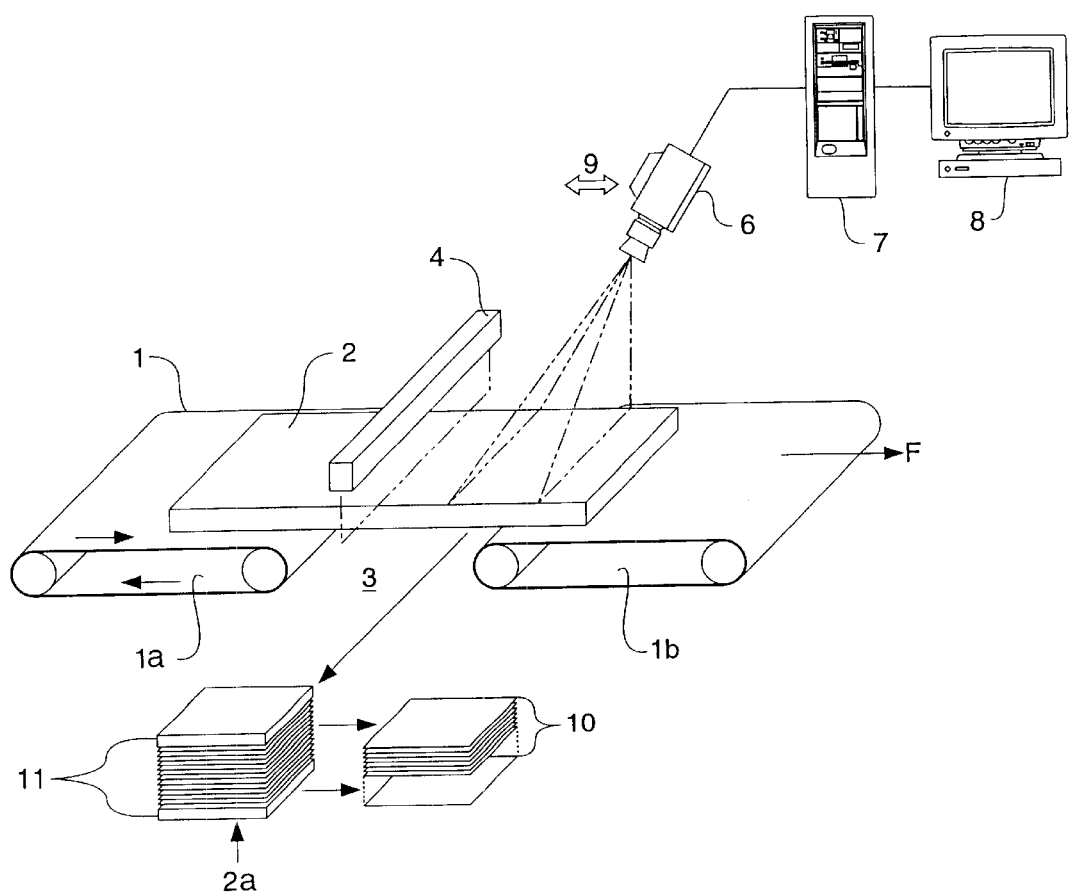
Fig_1_

DEVICE AND METHOD FOR NON-CONTACT DETECTION OF STRUCTURAL AND/OR SURFACE FAULTS IN LARGE SURFACE BODIES

APPLICATION CROSS REFERENCE

This application is a continuation of PCT Application No. PCT/DE99/02453 filed Aug. 5, 1999 and which named the United States as a designated country. PCT Application PCT/DE99/02453 was published on Apr. 20, 2000 as Publication No. WO 00/22423 and claims priority of German Application 198 46 995.0 filed on Oct. 13, 1998.

FIELD OF THE INVENTION

The present invention relates generally to material testing and, more particularly, to a device and method for non-contact detection of structural and/or surface faults in large-surface bodies.

BACKGROUND OF THE INVENTION

In the production of large-surface homogeneous materials, or those composed of various components, inclusion of air, cracks or inhomogeneities in he material itself or between the individual components may occur. These structural weaknesses generally reduce the adhesive power and therefore the quality of the product. It is therefore desirable to recognise these faults early on and if possible during the course of the manufacturing process, so as to be able to intervene in the manufacturing process to correct them.

Depending on the type and size of the material to be examined at the moment various procedures are used to detect weaknesses in material:

Systems which measure in points, such as, for example, ultrasound, radiometric, inductive or capacitive methods, give information on the weaknesses in a material in a small measuring field. To enable a 100% check of large-surface material with these methods, procedures measuring in points have to be conducted over the entire object, which is time-consuming. These procedures which measure in points are not usually suitable for use for a 100% on line manufacturing check because of the time-consuming scanning of the specimen. Simultaneous parallel operation of several appliances admittedly usually shortens measuring time, but makes the measuring devices correspondingly expensive.

Fast systems which measure surfaces extensively are desirable for 100% manufacturing control. Optical inspection of the surface in visible light allows, e.g. faults in the surface layer to be detected. Interferometric measuring systems, such as, e.g. the Electronic Speckle Model Interferometer (ESPI) or the Shear ESPI can measure the whole area for faults even inside material specimens. However, owing to their great sensitivity to outside disturbing influences they cannot be easily and reliably integrated into the production process. Microwaves or radio waves would in principle be suitable for a monitoring process of this kind, but require relatively high expenditure to comply with the strict safety regulations for use with sources of radiation.

DE 197 03 484 A1 discloses a test procedure in which internal faults are detected in a material or material composite, by the generation of a heat flow in the area to be examined, which is disrupted at defective spots. The resulting distortions of the surface temperature field are detected and evaluated for fault contrasting. The sensitivity to smaller, deeper lying internal faults is achieved by optimized heat conduction and by use of a high-resolution measuring device to detect the local and temporal surface temperature distribution.

DE 196 28 391 C1 discloses a signal-processing unit of a device for photothermal testing of a surface of a test sample. This provides a speed measuring device with which the relative speed of a test sample can be defined with regard to the optical part as well as a detector firmly attached thereto. With the thus gained measured speed value the temporal course of induced heat radiation generated by excitation radiation on a static test area can be corrected.

DE 197 20 461 A1 discloses a procedure and a device for monitoring the internal cooling structure of a turbine blade. An initial thermal image of the turbine blade to be tested is recorded by means of a first infrared camera. The turbine blade is then heated up for a short time by blowing hot air into its cooling structure. A thermal image of the thus heated up turbine blade is then recorded by a second infrared camera. The infrared thermal imaging camera can work in a line-scan mode, in other words scan the object by line. The temporal course of the temperature distribution recorded by the camera is digitalized on line by a personal computer by means of an appropriate evaluation and image-processing program and the initial thermal image subtracted therefrom in each case. These differential images are compared and assessed with pictures of a reference blade.

H. Tretout's treatise: "Composites, la thermographie ca marche en CND" MESURES, REGULATION AUTOMATISME, Vol. 51, No. 15, November 1986 (1986-11), pages 43–46, XP002125600 Paris, discloses a device in which the test sample is conveyed with the aid of a conveying device, not described in more detail, within a perpendicular plane past a horizontally radiating heat source and a thermal imaging camera positioned behind it, which has only one camera line.

The present invention is directed to overcoming one or more of the problems set forth above.

SUMMARY OF THE INVENTION

An aspect of the invention is to provide an improved procedure for non-contact detection of structural and/or surface faults in large surface bodies.

In accordance with the above aspect of the invention, there is provided a device that includes a conveying device with an approximately horizontal conveying plane and an unsupported area with respect to the test sample to be conveyed; a heat source arranged above the conveying plane over the unsupported area; a thermal imaging camera, which has several camera lines arranged in each case transversely to the direction of conveyance and in succession in the direction of conveyance, arranged above the conveying plane; and, a computer with monitor capable of using information recorded in succession from the camera lines to construct heat images coming from various depth planes of the test sample.

With the thermographic inspection appliance both defects on the surface of large board-shaped materials and also faults near the surface to a depth of several centimeters can be detected at great speed without contact and without destruction. This allows, for example, a thermographic picture of a coated chipboard to be produced, the surface of which has been homogeneously heated up a few degrees. After a short heat penetration time from each individual line of the thermal imaging surface camera a complex heat image model, rich in contrast, composed from various depth planes of the test sample, can be observed on the surface of the test sample. From these images conclusions can be drawn as to the quality of the gluing and the poor adhesive power of the material associated with it.

The above and other aspects, features and advantages of the present invention will become apparent from the following detailed description when taken in conjunction with the accompanying drawings.

BRIEF DESCRIPTION OF THE DRAWINGS

Reference is now made to the drawing, which illustrates the best presently known mode of carrying out the invention.

FIG. 1 is a schematic view of a non-contact detection device incorporating an embodiment of the present invention.

DETAILED DESCRIPTION

The device illustrated comprises a conveying device 1 for a large-surface, board-shaped test sample 2, which may, for example, be a coated chipboard. The schematically represented conveying device 1 is composed of two continuous conveyors 1a, 1b, spaced apart in the direction of conveyance F. The slight horizontal distance between these two continuous conveyors 1a, 1b forms an unsupported area 3 with respect to the test sample 2 to be conveyed. Above the unsupported area 3 and above the conveying plane a heat source 4, which radiates in lines or strips on to the conveying plane, is arranged as stationary and extending transversely to the direction of conveyance F. This arrangement minimizes any heating of the conveying device 1.

Positioned behind the heat source 4 in the direction of conveyance F is a thermal imaging camera constructed as a thermal imaging surface camera 6. The thermal imaging camera is also arranged in a stationary manner above the conveying plane and is directed with camera lines located transversely to the direction of conveyance F at the conveying plane. Connected to the thermal imaging camera is a computer 7, which constructs from every camera line a separate heat image model, which can be looked at on a color monitor 8 and evaluated on a PC.

The double arrow 9 shown in the FIGURE symbolizes an adjustment device for changing the distance to be measured in the direction of conveyance F between the heat source 4 and the thermal imaging camera 6.

The measurement is based on the discovery that the heat homogeneously introduced into the test sample disseminates at varying speed as a result of defects, cracks and/or inhomogeneities. With the thermal imaging camera the different heat image models developing after a while according to the heat conduction of the material and the depth of the defect can be observed on the surface.

The speed of conveyance of the test sample 2, the distance between the heat source 4 and the surface of the test sample 2, as well as the power of the heat source 4, determine the desired energy input into the test sample. All three of these variables may be modified with separate adjusting devices.

The actual inspection of the test sample 2 takes place—seen in direction of conveyance F—behind the heat source 4 with a thermal imaging camera, which is equipped as a complete surface camera (Focal Plane Array) and is attached at such a height above the test sample to be measured that with the appropriate optics the desired width of the surface of the test sample 2 is imaged. The individual lines of this surface camera are herein arranged transversely to the direction of conveyance F and in succession in the direction of conveyance F. The depth layer of the test sample 2 to be examined is determined by the setting of the distance of the thermal imaging camera 6 with respect to the heat source 4 in conjunction with the speed of the conveying device 1. If the camera is located closely behind the heat source 4, it records heat images of layers close to the surface. If the distance of the camera from the heat source 4 is enlarged, the heat image model of the surface of the test sample presents a signal from deeper layers, as the heat radiated from the heat source 4 has already been able to penetrate more deeply into the test sample 2 because of the extended conveyance path.

Because of the even through movement of the test sample 2 under the surface camera 6 a separate image of the test sample 2 is constructed out of every camera line in the connected computer 7 and its monitor 8. This creates as many heat images of the test sample as the camera has lines. As every camera line records a slightly more remote area of the test sample 2 from the heat source 4, the respective line images contain information from various depth planes 10 of the test sample 2, as indicated diagrammatically in the bottom part of the FIGURE. Cutout 2a shows n-lines 11 which relay information from various depth planes 10.

In this way with a thermal imaging surface camera 6 it is possible simultaneously to record the signal from various depths of a test sample.

While a preferred embodiment of the present invention has been illustrated and described, this has been by way of illustration and the invention should not be limited except as required by the scope of the appended claims.

We claim:

1. A device for non-contact detection of structural and/or surface faults in large-surface bodies, comprising:
   a conveying device having a generally horizontal conveying plane and an unsupported area with respect to the large-surface bodies conveyed thereby;
   a heat source located above the conveying plane and disposed over the unsupported area, the heat source extending transversely to a direction of conveyance and for radiating heat toward the conveying plane;
   a thermal imaging camera positioned above the conveying plane and directed at the conveying plane, said thermal imaging camera having several camera lines arranged in succession and extending transversely to the direction of conveyance; and
   a computer and a monitor for processing information recorded in succession from the camera lines of the thermal imaging camera and constructing heat image models of various depths of the large-surface bodies.

2. The non-contact detection device as set forth claim 1, wherein the conveying device includes two spaced continuous conveyors to create the unsupported area of the conveying device in the area of the heat source.

3. The non-contact detection device as set forth in claim 1, including an adjustment device for changing the distance between the heat source and the thermal imaging camera in the direction of conveyance.

4. The non-contact detection device as set forth in claim 1, including an adjustment device for changing the speed of the conveying device.

5. The non-contact detection device as set forth in claim 1, including an adjustment device for changing the distance of the heat source from the conveying plane.

6. The non-contact detection device as set forth in claim 1, including means for adjustment the power delivered to the heat source.

7. A device for non-contact detection of structural and/or surface faults in large-surface bodies, comprising:
   a conveying device having a generally horizontal conveying plane and an unsupported area with respect to the large-surface bodies conveyed thereby, the conveying device including two spaced continuous conveyors to create the unsupported area, and means for changing the speed of the conveying device;

a heat source located above the conveying plane and disposed over the unsupported area, the heat source extending transversely to a direction of conveyance and for radiating heat toward the conveying plane, the heat source including means for changing the distance of the heat source from the conveying plane, and means for adjustment the power delivered to the heat source;

a thermal imaging camera positioned above the conveying plane and directed at the conveying plane, said thermal imaging camera having several camera lines arranged in succession and extending transversely to the direction of conveyance;

an adjustment device for changing the distance between the heat source and the thermal imaging camera in the direction of conveyance; and a computer and a monitor for processing information recorded in succession from the camera lines of the thermal imaging camera and constructing heat image models of various depths of the large-surface bodies.

8. A method for non-contact detection of structural and/or surface faults in large-surface bodies, comprising:

conveying the large-surface bodies in one direction;

heating the large-surface bodies with a heat source spaced therefrom;

after heating, taking thermal images of the large-surface bodies using a thermal imaging camera having several camera lines arranged in succession and transverse to said one direction; and constructing heat image models of various depth planes of the large-surface bodies using a computer that processes information recorded in succession from the camera lines to construct said heat image models.

* * * * *